(12) United States Patent
Dennis

(10) Patent No.: US 6,517,549 B1
(45) Date of Patent: Feb. 11, 2003

(54) MEDICAL MOUTHPIECE WITH ELLIPTICAL PASSAGEWAY

(75) Inventor: William G. Dennis, Jacksonville, FL (US)

(73) Assignee: Core Dynamics, Inc., Jacksonville, FL (US)

(*) Notice: Subject to any disclaimer, the term of this patent is extended or adjusted under 35 U.S.C. 154(b) by 0 days.

(21) Appl. No.: 09/938,339

(22) Filed: Aug. 24, 2001

(51) Int. Cl.⁷ ................................................ A61F 11/00
(52) U.S. Cl. .................... 606/108; 600/237; 128/200.26
(58) Field of Search ................................ 600/237, 238, 600/239, 240; 606/108, 1; 128/207.14, 207.17, 200.26; 604/171, 179, 264, 270

(56) References Cited

U.S. PATENT DOCUMENTS

| | | | |
|---|---|---|---|
| 1,657,148 A | * 1/1928 | De Forest | 600/237 |
| 4,944,313 A | 7/1990 | Katz et al. | |
| 5,092,346 A | 3/1992 | Hays et al. | |
| 5,174,284 A | * 12/1992 | Jackson | 128/200.26 |
| 5,251,616 A | * 10/1993 | Desch | 128/200.26 |
| 5,267,984 A | * 12/1993 | Doherty | 604/283 |
| 5,277,202 A | 1/1994 | Hays | |
| 5,499,633 A | 3/1996 | Fenton | |
| 5,590,643 A | * 1/1997 | Flam | 128/200.26 |
| 5,806,516 A | * 9/1998 | Beattie | 128/207.17 |
| 5,934,276 A | * 8/1999 | Fabro et al. | 128/207.17 |
| 6,129,084 A | 10/2000 | Bergersen | |

FOREIGN PATENT DOCUMENTS

| | | |
|---|---|---|
| JP | 7-51154 | 6/1995 |
| JP | 7-17289 | 8/1996 |
| JP | 2000-325302 | 11/2000 |

* cited by examiner

Primary Examiner—Eduardo C. Robert
(74) Attorney, Agent, or Firm—Hunton & Williams

(57) ABSTRACT

The present invention provides a mouthpiece assembly for establishing a protected airway for a patient. The mouthpiece assembly comprises a generally elliptical tubular bite block having a generally elliptical passageway formed therethrough. The mouthpiece assembly further comprises a generally elliptical front shield attached to the front end of the tubular bite block portion. The front shield has a central opening in communication with the passageway for receiving medical instruments therethrough and a strap opening adjacent each of the opposing edge portions. At least a portion of the front shield is curved rearward and is flexible to allow the at least a portion of the front shield to conform to the patient's facial structure. The mouthpiece assembly also comprises a tongue depressing member extending rearwardly and downwardly from the rearward end of the bottom wall of the tubular bite block, and a resilient cushioning sleeve formed around at least a portion of the tubular bite block. A headstrap has an elongate belt member adapted for insertion through the strap openings to connect the belt ends to the front shield.

33 Claims, 10 Drawing Sheets

MEDICAL MOUTHPIECE WITH ELLIPTICAL PASSAGEWAY

FIELD OF THE INVENTION

This invention relates generally to oral airway devices and more particularly to a mouthpiece having an elliptical passageway adapted for receiving a variety of medical instruments.

BACKGROUND OF THE INVENTION

Medical treatment often requires the maintenance of a clear airway for the delivery of oxygen or general anesthesia. Esophageal tubes inserted through a patient's mouth and into the esophagus are typically used to assure uninterrupted delivery of oxygen or anesthetic gas. However, such tubes are relatively pliable and may susceptible to inadvertent closure due to the clamping down of a patient's teeth on the tube. There may also be a tendency for accidental removal of the tube due to patient movement or deliberate action. It is therefore desirable to provide protective elements that prevent removal or closure of such tubes.

In addition, certain medical procedures require the introduction of instruments through the mouth without interference from the patient's teeth and tongue. Endoscopes and other diagnostic instruments may have relatively fragile components that must be protected from damage due to the clamping action of the patient's teeth. At the same time, it is highly desirable to protect the tissue in and around the patient's mouth as well as the patient's tongue, teeth and gums from damage due to the insertion of diagnostic instruments through the mouth.

It is also desirable to prevent retraction of an unconscious patient's tongue because such retraction can stimulate the patient's gag reflex or cause a blockage of the patient's airway.

SUMMARY OF THE INVENTION

There is therefore a need for an apparatus that protects the integrity of esophageal tubing or other instruments inserted through the mouth into the esophagus and to protect the patient from injury caused by the insertion of such instruments. In addition, there is a need to prevent the blockage of a patient's airway due to retraction of the tongue.

Accordingly, an embodiment of the present invention provides a mouthpiece assembly for establishing a protected airway for a patient. The mouthpiece assembly comprises a generally elliptical tubular bite block having a substantially vertical minor axis extending between opposing top and a bottom walls and having opposing forward and rearward ends and a generally elliptical passageway formed therethrough. The mouthpiece assembly further comprises a generally elliptical front shield attached to the front end of the tubular bite block portion. The front shield has a generally horizontal major axis extending between opposing edge portions, a central opening in communication with the passageway for receiving medical instruments therethrough and a strap opening adjacent each of the opposing edge portions. At least a portion of the front shield is curved rearward and is flexible to allow the at least a portion of the front shield to conform to the patient's facial structure. The mouthpiece assembly still further comprises a tongue depressing member extending rearwardly and downwardly from the rearward end of the bottom wall of the tubular bite block. The tongue depressing member is adapted for engaging the tongue of the patient and substantially preventing a forward portion of the tongue from moving rearward and blocking the patient's airway. The mouthpiece assembly also comprises a resilient cushioning sleeve formed around at least a portion of the tubular bite block, the resilient cushioning sleeve formed of a closed cell foam material. The cushioning sleeve is adapted for receiving and engaging the patient's upper and lower teeth and the patient's upper and lower lips. The mouthpiece assembly may also comprise a substantially cylindrical plug formed from a resilient closed cell foam material. The plug is adapted for compression and insertion into the passageway to position and secure an instrument inserted through the passageway. The mouthpiece assembly may also comprise a headstrap having an elongate belt member with first and second ends adapted for insertion through the strap openings in the front shield and for fastening the belt member to the front shield. The belt member is adapted for engaging the back of the patient's head to secure the mouthpiece assembly in place.

Other objects and advantages of the invention will be apparent to one of ordinary skill in the art upon reviewing the detailed description of the invention.

DETAILED DESCRIPTION OF THE INVENTION

Figure 1:
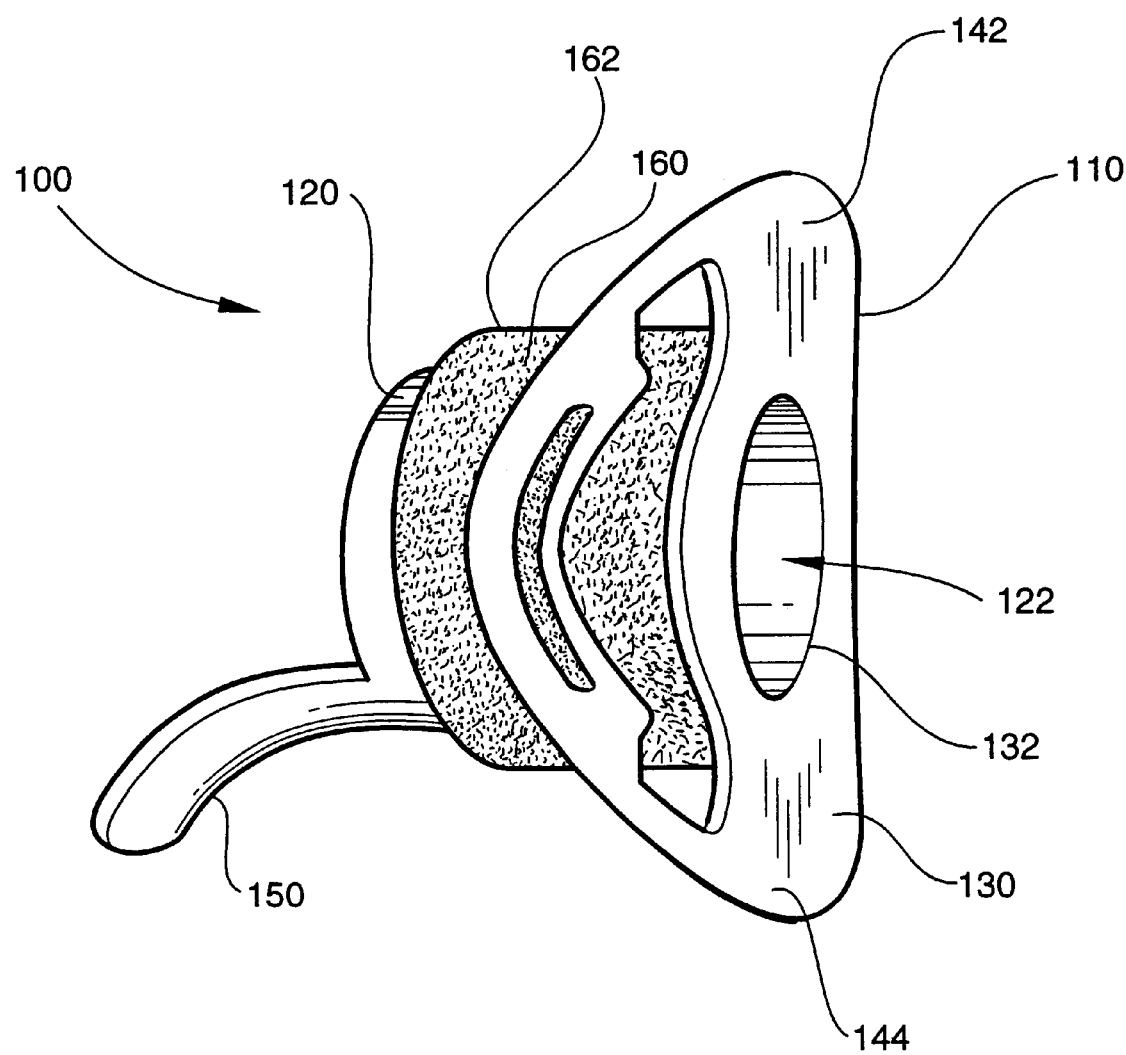
FIG. 1 is a perspective view of a mouthpiece assembly according to an embodiment of the invention.
Figure 2:
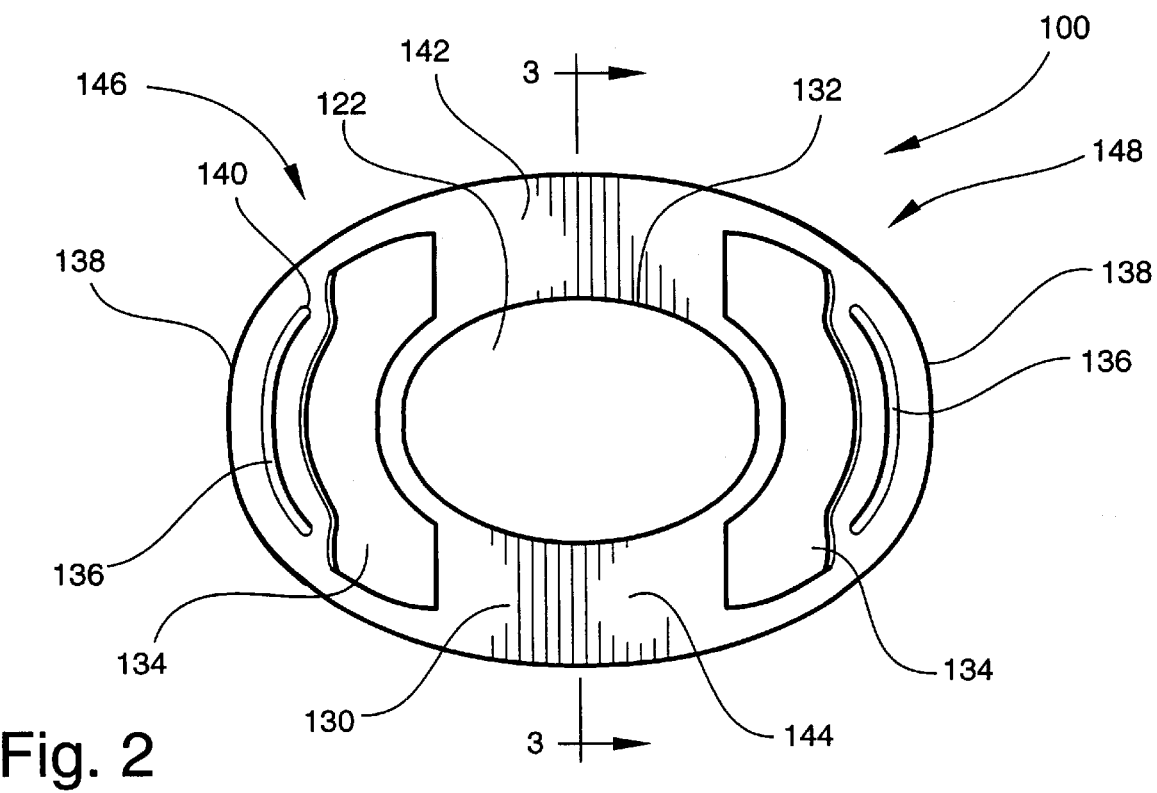
FIG. 2 is a front view of the mouthpiece assembly of FIG. 1.
Figure 3:
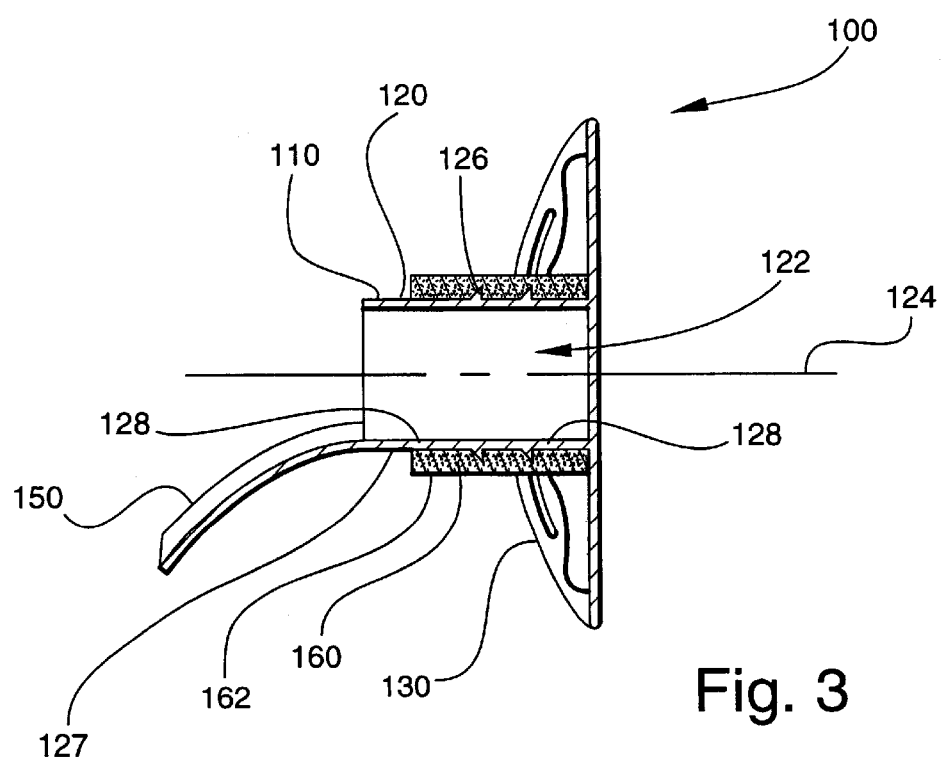
FIG. 3 is a section view of the mouthpiece assembly of FIG. 1.
Figure 4:
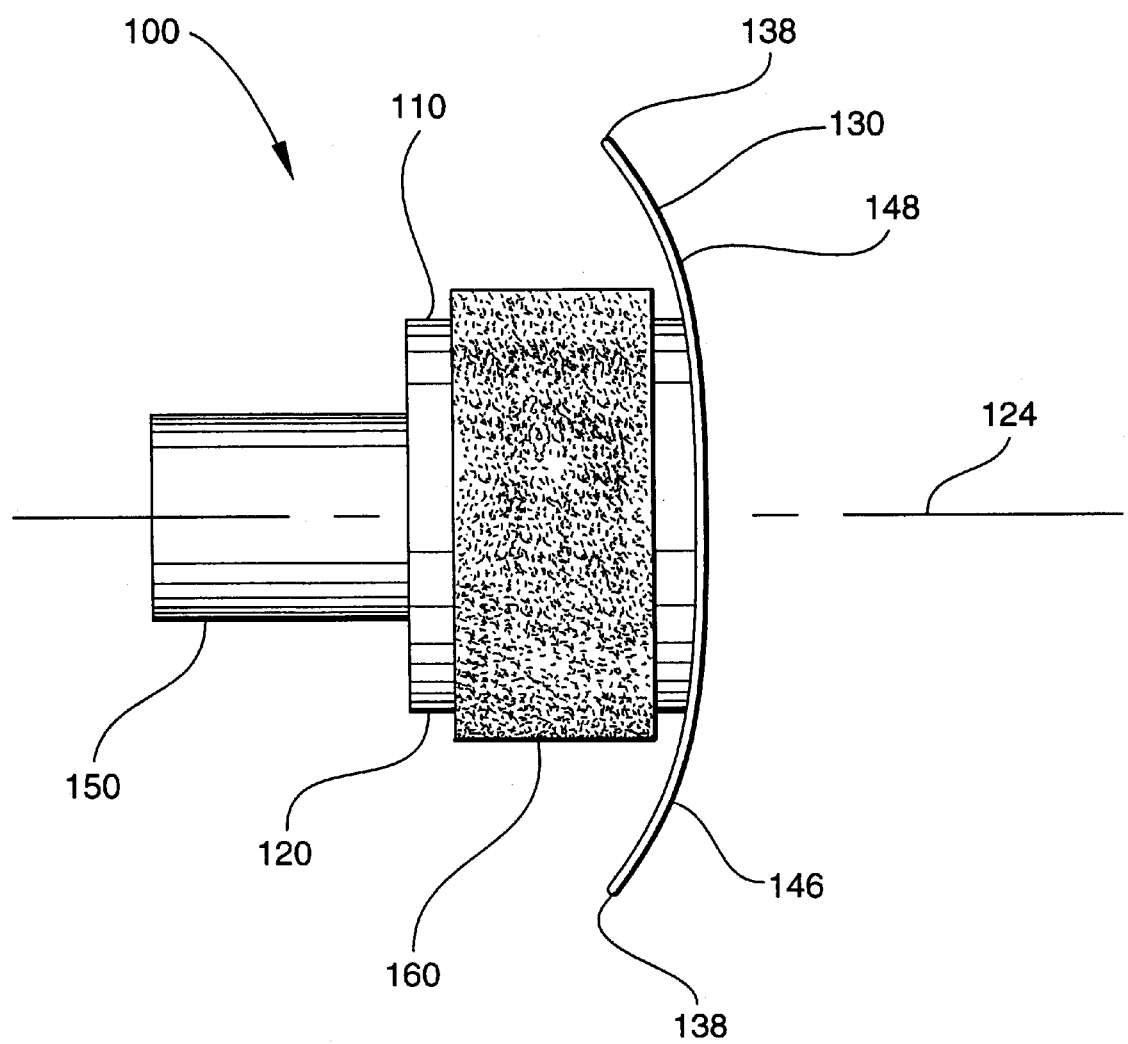
FIG. 4 is a top view of the mouthpiece assembly of FIG. 1.

The present invention provides a mouthpiece assembly that is clampable between the front teeth of a patient that is to receive medical instruments or tubes through the mouth and into the esophagus. As shown in FIG. 1, a mouthpiece assembly 100 according to the present invention includes a main body 110 having a tubular bite block portion 120, a front shield 130 and a tongue depressing member 150. The assembly 150 also includes a tubular foam cushion 160 surrounding the forward portion of the bite block 120. The bite block 120 has a passageway 122 formed therethrough for receiving instruments or tubing therethrough.

Referring now to FIGS. 1–4, the mouthpiece of the present invention will be described in more detail. The bite block 120 is formed as a generally elliptical tube with the major axis of its elliptical cross-section being generally horizontal and the minor axis being generally vertical. The elliptical shape of the bite block tube 120 is generally similar to the shape of a patient's mouth and is sized to be comfortably received between the upper and lower teeth of the patient. The bite block 120 is formed as a rigid structure that will not be significantly deformed by the clamping of a patients teeth.

The passageway 122 formed by the bite block tube 120 is also generally elliptical and has a centerline 124. In one exemplary embodiment of the invention, the major axis of the elliptical passageway 122 is 3.3 cm. long and the minor axis is about 2.1 cm. long. The shape and dimensions of the passageway 122 provides the capability of receiving instruments and tubing with a variety of cross-sectional shapes and sizes. For example, the passageway 122 can easily accommodate a 60 FR dilator. Suction tubes may also be used in conjunction with the mouthpiece assembly 100.

The main body 110 includes a flange-like front shield 130 attached to the forward end of the bite block tube 120. The front shield 130 is generally elliptical or oval in shape and has an elliptical central opening 132 surrounding the entrance to the passageway 122. The major axes of the front shield 130 and the central opening 132 are both generally horizontal and the minor axes are both generally vertical. The front shield 130 is formed as a thin, generally symmetric, elliptical member that curves slightly rearward on both sides of the central opening 132. The curvature of the front shield 130 is provided to generally conform to the curvature of a patient's face to provide comfort and to protect the area surrounding the patient's mouth. The front shield 130 includes upper and lower shield areas 142, 144 that are substantially rigid and protect the upper and lower lips of the patient. Two cutout areas 134 are sized and configured to provide flexibility to the side areas 146, 148 of the shield 130. The added flexibility allows the front shield 130 to adapt to the facial structure of the individual patients. The use of the cutouts 134 also reduces the amount of material required to manufacture the front shield 130. The front shield 130 also includes two curved strap openings 136 near the edges 138 of the left and right sides 146, 148 of the shield. These strap openings 136 are used in conjunction with a strap 180 to hold the mouthpiece assembly 100 in place as will be discussed in more detail hereafter.

The main body 110 of the mouthpiece assembly 100 includes a tongue depressing member 150 that extends rearward from the bottom wall 127 of the bite block at the rear end of the bite block tube 120. The tongue depressing member 150 has a shallow C-shaped cross-section that provides a smooth transition from the elliptical curvature of the lower wall 128 of the passageway 122. The tongue depressing member 150 is substantially rigid and has a downward curve that is configured to depress the patient's tongue and to guide the forward end of instruments inserted through the passageway 122. The tongue depressing member 150 prevents the retraction of the forward portion of the patient's tongue, which could otherwise cause a blockage of the patient's airway. The tongue depressing member 150 is sized so that it fits between the rear teeth of the patient and so that it does not instigate the gag reflex of the patient.

The bite block tube 120, front shield 130 and tongue depressing member 150 may be formed from polyethylene, polypropylene or other similar medical-grade plastic and may be integrally formed as a single body. The surfaces of the main body components and, in particular, the surface of the passageway 122 should be smooth to assure low friction when instruments are inserted through the mouthpiece assembly 100.

The mouthpiece assembly 100 of the invention includes a relatively soft cushioning layer 160 that surrounds at least a portion of the bite block tube 120. The cushioning layer 160 provides a cushion for the teeth, lips and tongue of the patient to engage when the mouthpiece is installed. The cushioning layer 160 may be formed as an annular sleeve 162 that may be stretched to fit over the bite block tube 120. The bite block tube 120 may include wedge-shaped detents 126 that serve to hold the cushioning sleeve 162 in place. These detents 126 each have a rearward-facing ramp and a substantially vertical forward face. This configuration allows the cushioning sleeve 162 to slide forward relatively easily onto the bite block tube 120 but prevents the cushioning sleeve 162 from sliding rearward once it is in place. It will be understood that other mechanisms for securing the cushioning sleeve 162 may also be used including ridges, teeth, threads or other suitable detents. The detents may be located on opposing sides of the bite block tube 120 or at regular intervals around the circumference of the tube 120.

The cushioning layer 160 may be formed using a closed cell foam or other similar material. The closed cell nature of the foam retains its resilience and provides superior cushioning properties.

Figure 5:
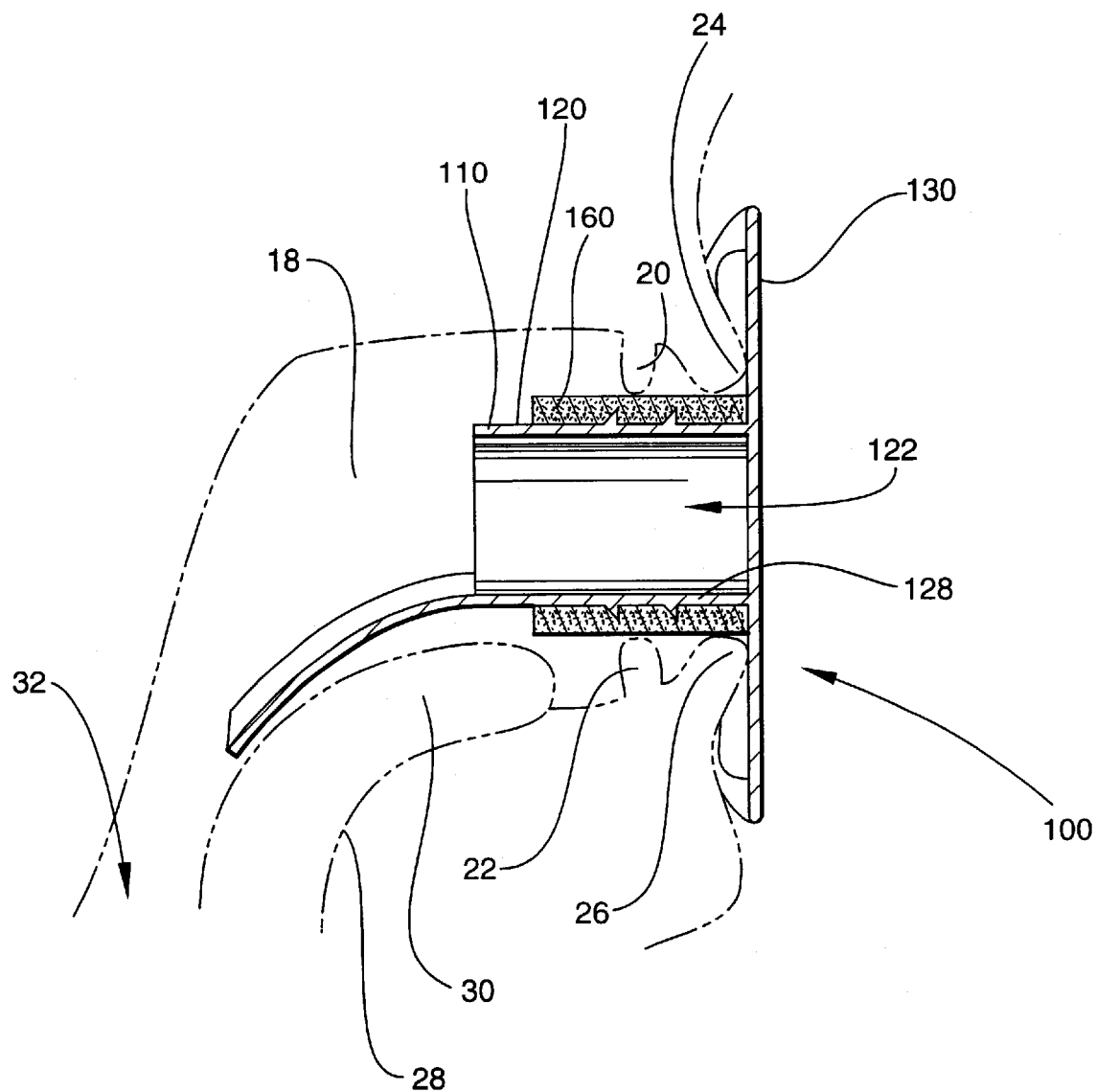
FIG. 5 is a section view of the mouthpiece assembly of FIG. 1 with the mouthpiece installed in a patient's mouth.
Figure 6:
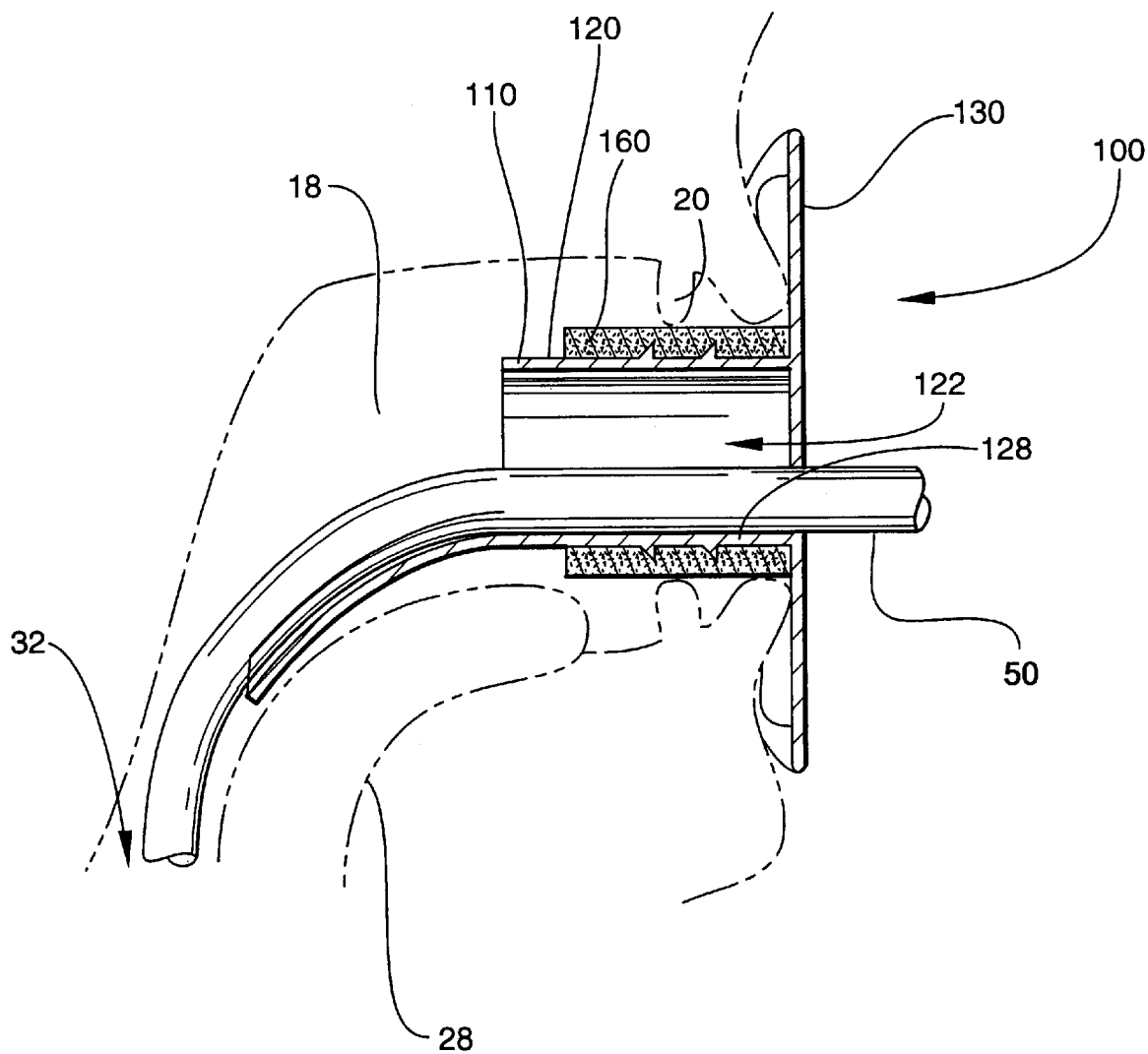
FIG. 6 is a section view of the mouthpiece assembly of FIG. 1 with a tube inserted therethrough.

FIG. 5 illustrates the mouthpiece assembly 100 in place within a patient's mouth cavity 18. With the assembly 100 in place, the patient's upper teeth 20 and lower teeth 22 engage the cushioning layer 160 surrounding the bite block tube 120. The upper and lower lips 24, 26 of the patient engage the cushioning layer 160 adjacent the front shield 130. The tongue depressing member 150 engages the patient's tongue 28 and, as previously described, prevents the forward portion 30 of the tongue 28 from moving rearward. As shown in FIG. 6, a tube 50 or other instrument can be inserted into the passageway 122 and may be guided into the patient's esophagus 32 by the tongue depressing member 150.

Figure 7:
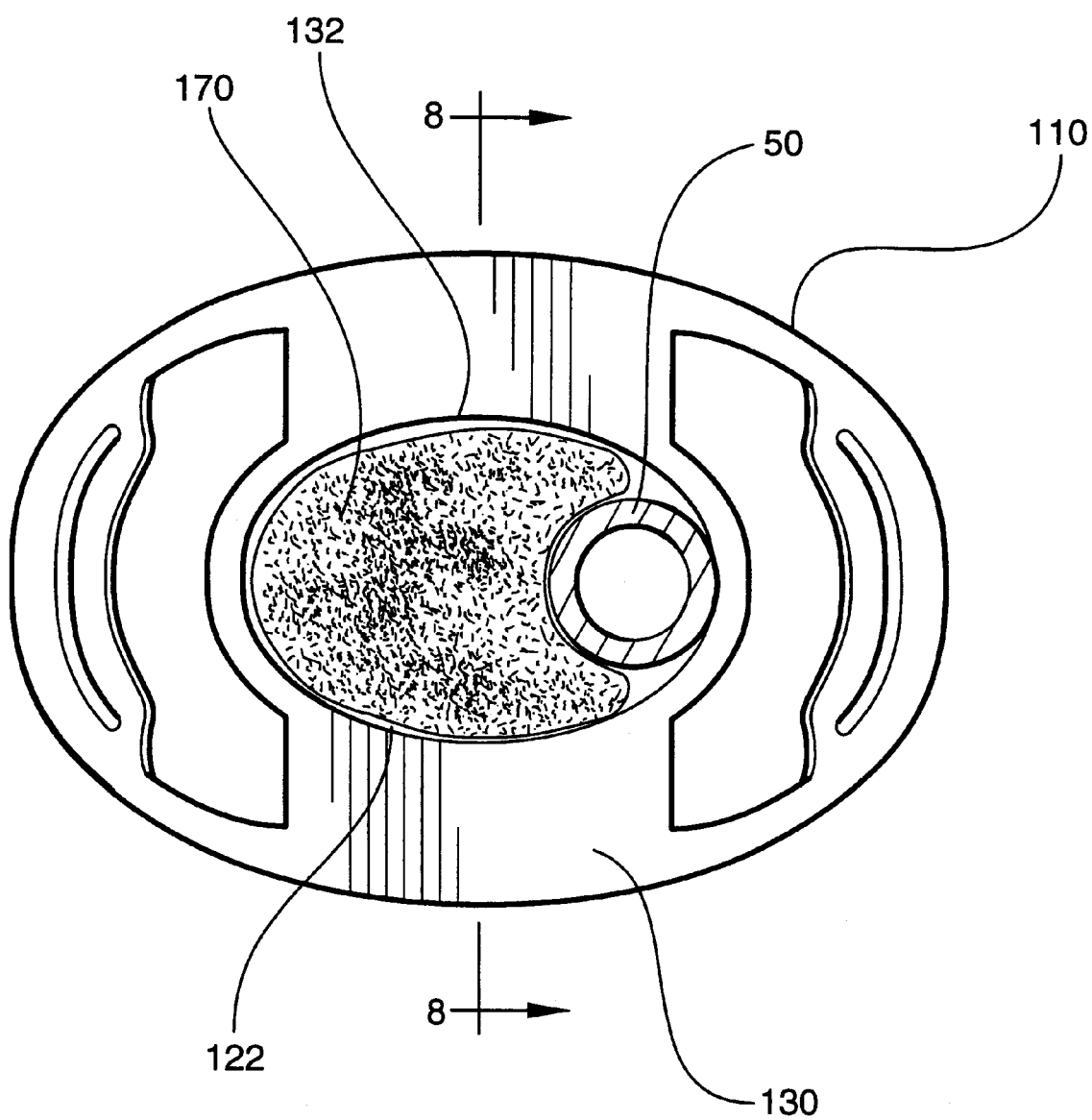
FIG. 7 is a front view of mouthpiece assembly according to the invention with a tube and a plug inserted in the passageway of the mouthpiece assembly.
Figure 8:
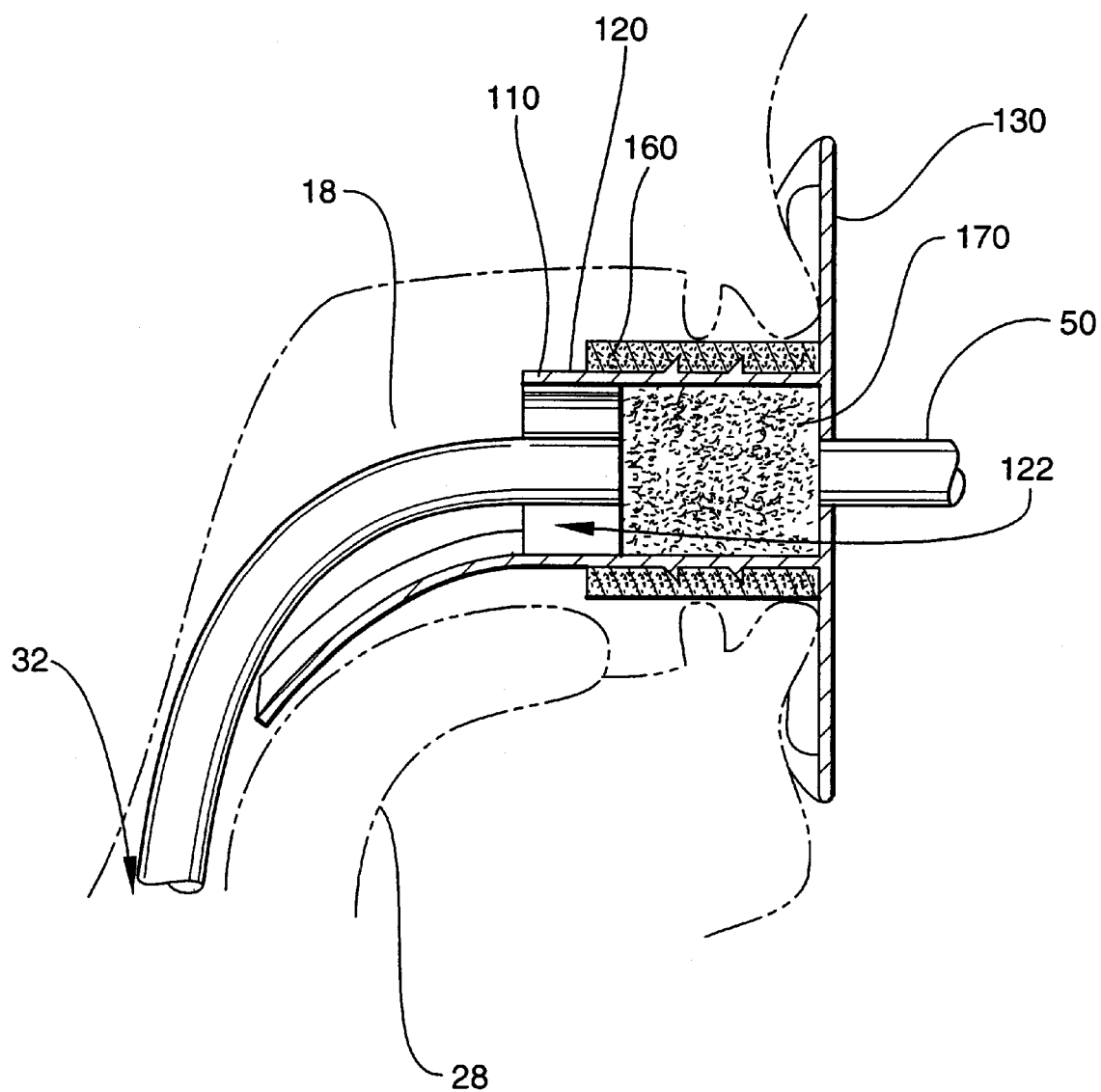
FIG. 8 is a section view of the mouthpiece assembly of FIG. 7.

The elliptical shape of the passageway 122 provides medical personnel a high degree of flexibility with respect to the insertion and placement of tubes or instruments. As shown in FIG. 6, the tube 50 is essentially centered and resting on the bottom of the passageway 122. As shown in FIGS. 7 and 8, however, the tube 50 may be positioned to one side of the elliptical passageway 122.

It will be understood by those having ordinary skill in the art that, depending on the circumstances, the mouthpiece assembly 100 may be inserted either before or after a tube 50 or other instrument is inserted. The mouthpiece assembly 100 may, for example, facilitate the insertion and use of certain instruments and therefore would be inserted prior to the insertion of such instruments. Other tubes or instruments may require insertion before the mouthpiece assembly 100. Esophageal tubes, for example, may often be inserted prior to the mouthpiece assembly 100. The present invention is particularly useful in such an instance, because the size and shape of the passageway 122 allow it to pass over the flange that is typically positioned at the proximal end of the tube for connection of the tube to other gas lines. Thus, the mouthpiece assembly 100 can be inserted with an esophageal tube in place.

One aspect of the invention provides a resilient plug 170 that can be inserted into the passageway 122 alongside the tube 50 to hold the tube 50 in place. The plug 170 is a generally elliptical cylinder formed of a deformable material such as a closed cell foam. The elliptical cross-section of the plug 170 is sized so that the plug 170 must be compressed slightly in order to allow insertion of the plug 170 into the passageway 122. Once inserted, the resiliency of the foam plug 170 provides an outward force against the wall of the passageway 122, which lodges the plug 170 in place within the passageway 122. As is shown in FIG. 7, the plug 170 can be deformed and squeezed into the passageway 122 in such a way that it conforms to the inner surface of the passageway 122 and any instrument or tube disposed therein. The plug 170 serves to prevent the tube 50 or other instrument from moving from side-to-side and also resists movement of the tube 50 inward or outward. This feature is facilitated if the plug 170 is sized to be slightly larger than the passageway 122 but with relative dimensions (i.e., a ratio of minor axis to major axis) similar to those of the passageway 122.

Using the plug 170, the tube 50 may be positioned anywhere along the inner surface of the passageway 122. In an alternative embodiment (not shown), a plurality of smaller plugs may be used to position a tube or instrument within the passageway. In another alternative embodiment, an annular plug having a central passageway formed therethrough could be used to centrally locate the tube 50 within the passageway 122. Alternatively a centering membrane or valve--such as a septum valve or duckbill valve--could be disposed within the passageway 122 for use in positioning and securing the tube 50 or other instrument.

Figure 9:
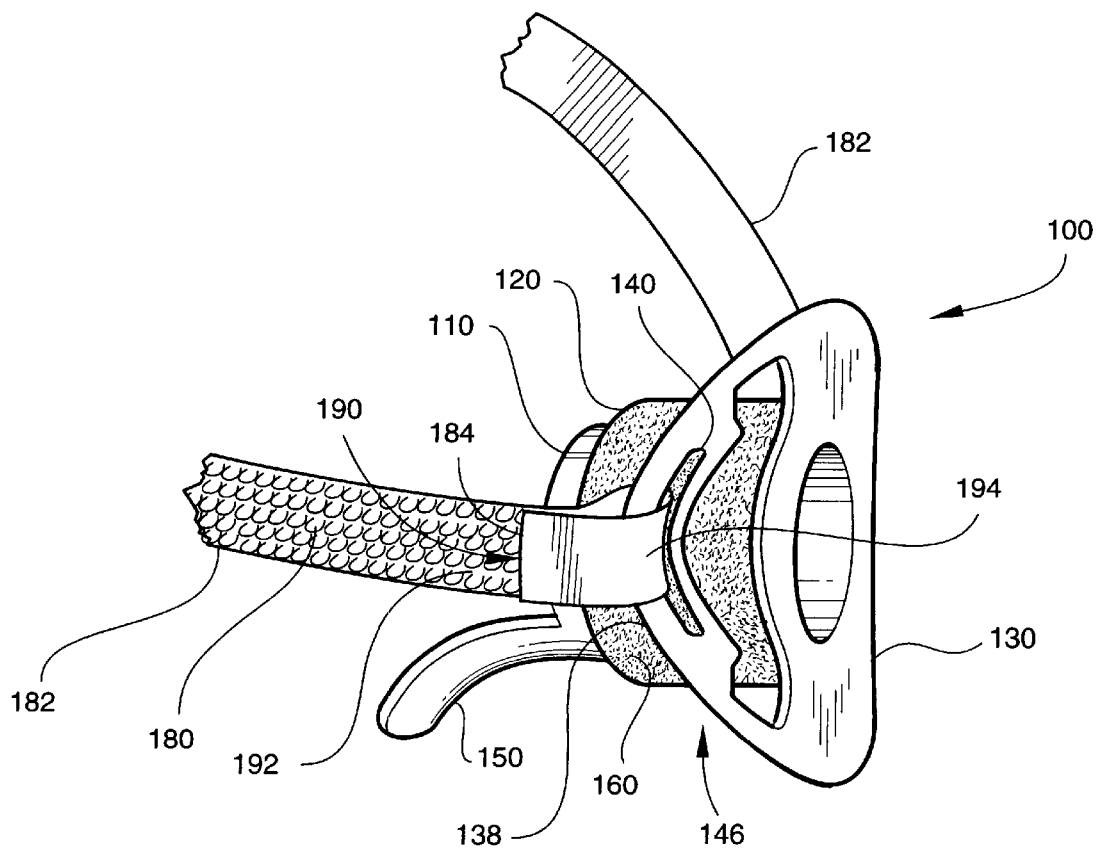
FIG. 9 is a perspective view of a mouthpiece assembly with a headstrap according to an embodiment of the invention.
Figure 10:
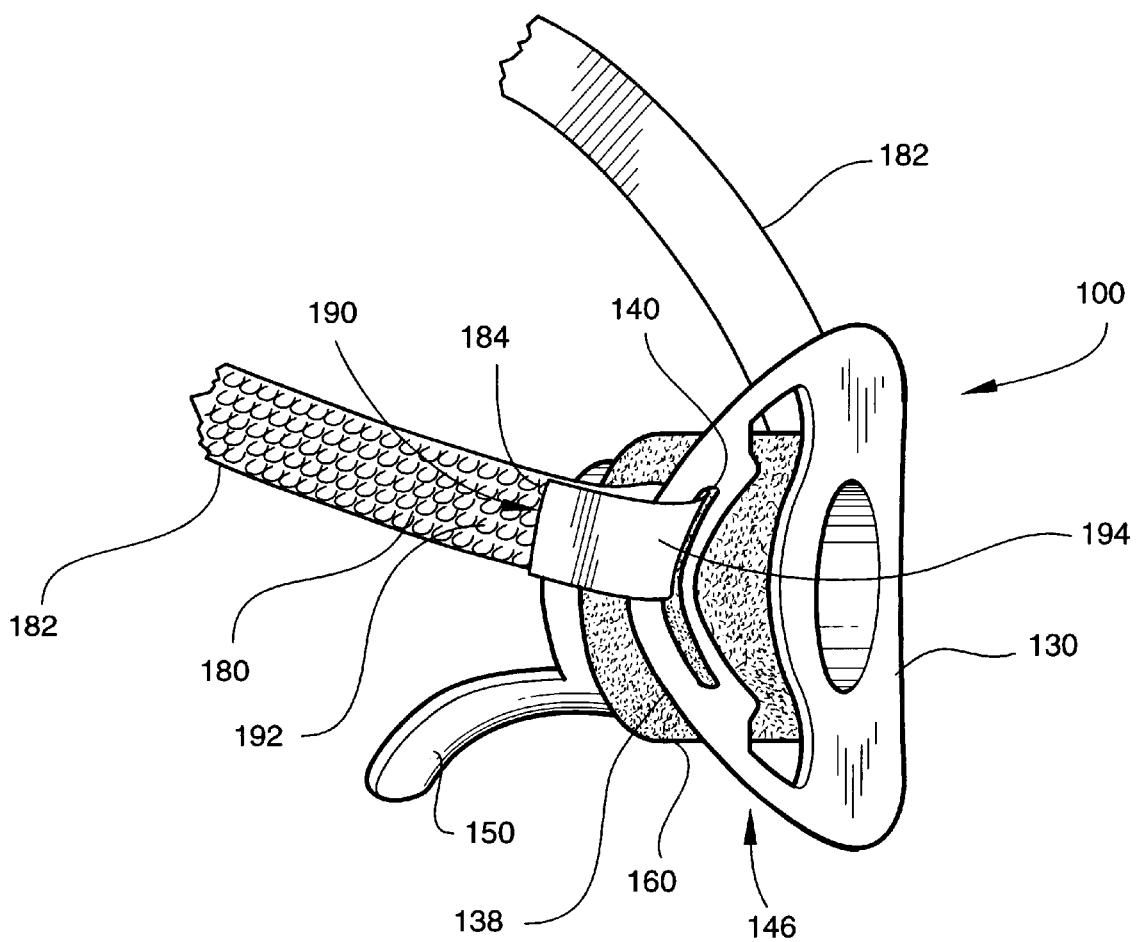
FIG. 10 is another perspective view of the mouthpiece assembly of FIG. 9.
Figure 11:
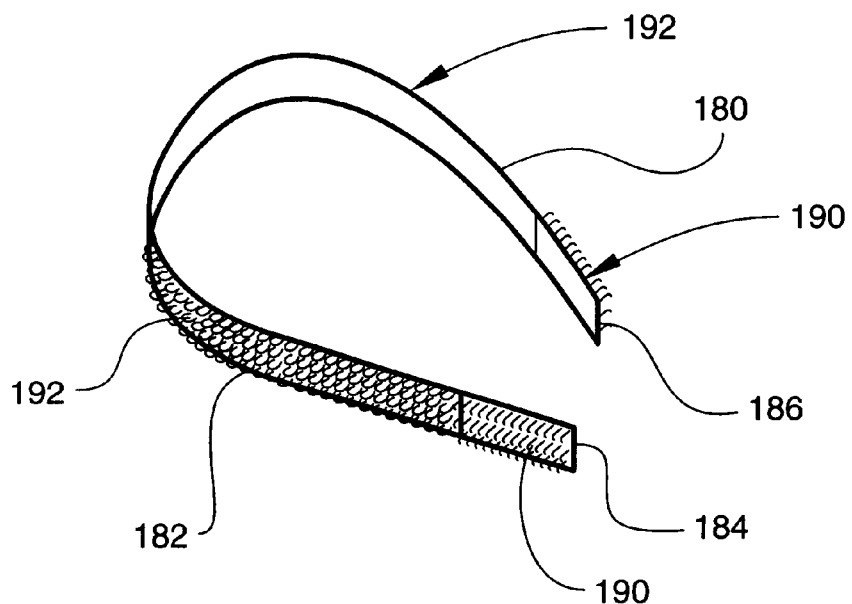
FIG. 11 is a perspective view of headstrap that can be used in a mouthpiece assembly of the present invention.

With reference to FIGS. 9–11, a mouthpiece assembly 100 according to the present invention may include a headstrap 180 that attaches to the sides 146, 148 of the front shield 130 and wraps around the back of the patient's head to secure the mouthpiece assembly 100 in place. The headstrap 180 includes an elongate belt member 182 formed of a thin pliant material. The belt member 182 may be a woven fabric and is preferably non-stretchable to assure stability. The headstrap 180 includes a hook-and-loop fastener 188 near each end 184, 186 of the belt member 182. The hook-and-loop fastener 188 includes a hook portion 190 adjacent each end 184, 186 and a loop portion 192 adjacent the hook portion and extending along the outer surface of the belt member 182. As shown in FIG. 9, the ends 184, 186 of the belt member 182 are threaded through the strap openings 136 on opposite sides 146, 148 of the front shield 130 then bent around the outer edge portion 138 of the shield 130. The ends 184, 186 are arranged so that after wrapping around the edge portion 138, the hook portion 190 may be brought in opposition with the loop portion 192 for mating engagement therewith. When the mouthpiece assembly 100 is inserted, one end 184 or 186 of the headstrap 180 may be inserted and fastened to the front shield 130 and the belt member 182 wrapped around the back of the patient's head to allow the other end 184 or 186 to be inserted and fastened to the front shield 130. It will be understood by those of ordinary skill in the art that the configuration of the hook-and-loop fasteners 188 allow infinite adjustment of the headstrap 180 which can thus be firmly secured regardless of the size of the patient's head.

It will be understood by those of ordinary skill in the art that other fasteners may be used to secure the ends 184, 186 of the headstrap 180 to the front shield 130. These may include, but are not limited to, snaps, buckles, knots and clasps. It will also be understood that a headstrap having two belt members may be used. In such an embodiment, the two belt members would require a clasp or buckle to connect the belt members to form a single tension member for the mouthpiece assembly 100.

Once secured, the headstrap 180 prevents the mouthpiece assembly 100 from being inadvertently removed or dislodged. The rearward tension on the outer edges 138 of the front shield 130 caused by the headstrap 180 also assists in forcing the flexible side areas 146, 148 of the front shield to conform to the patient's facial structure. An advantageous feature of the invention is that the curved strap opening 136 may allow a small amount of movement of the fastened end 194 of the headstrap 180 but prevents a large amount of movement that would result in a slackening of the headstrap 180. As shown in FIG. 10, the fastened end 194 can be moved around the edge 138 of the front shield 130 until hitting the end 140 of the strap opening 136. This allows for a range of adjustment for comfort of the headstrap 180 without allowing the possibility of the mouthpiece assembly 100 being dislodged.

Figure 12:
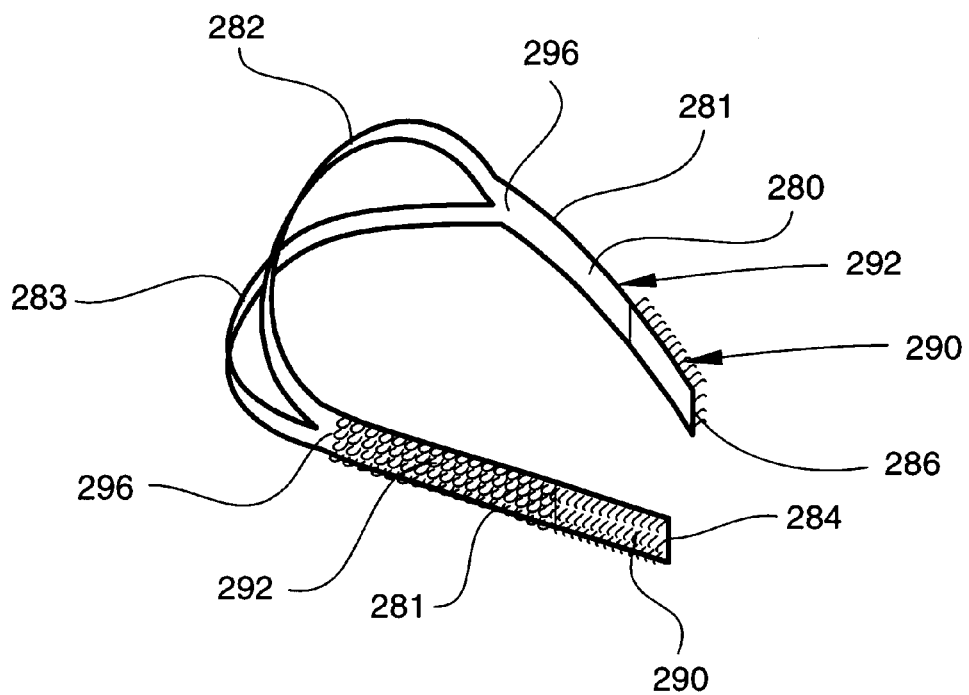
FIG. 12 is a perspective view of another headstrap that can be used in a mouthpiece assembly of the present invention.

FIG. 12 illustrates a headstrap 280 that can also be used in conjunction with the present invention. The headstrap 280 attaches to the sides 146, 148 of the front shield 130 and wraps around the back of the patient's head to secure the mouthpiece assembly 100 in place. The headstrap 280 includes two side belt members 281, an upper rear belt member 282 and a lower rear belt member 283, all formed of a thin pliant material. The belt members 281–283 may be a woven fabric and are preferably non-stretchable to assure stability. The headstrap 280 includes a hook-and-loop fastener 288 near each end 284, 286 of the headstrap 280. The hook-and-loop fastener 288 includes a hook portion 290 adjacent each end 284, 286 and a loop portion 292 adjacent the hook portion and extending along the outer surface of the side belt members 181. The side belt members 281 each terminate at a Y-joint 296 where the side belt members 281 are connected to opposite ends of the upper and lower rear members 282, 283. The upper and lower rear members 282, 283 are configured to diverge from each other as they depart one Y-joint and encircle the back of the patient's head, then converge as they approach the opposite Y-joint 296. This provides a wider distribution of the load required to keep mouthpiece assembly 100 in place and provides a higher degree of stability. The headstrap 280 is fastened in a manner substantially similar to that described above for the headstrap 180 illustrated in FIG. 11.

It will be understood that the components of the present invention can be provided in varying size ranges to accommodate patients of varying age and size. The relative sizes of the components may also be varied to accommodate patients with unusual problems or requirements.

Other embodiments and uses of the invention will be apparent to those skilled in the art from consideration of the specification and practice of the invention disclosed herein. The specification and examples should be considered exemplary only. The scope of the invention is limited only by the claims appended hereto.

What is claimed is:

1. A mouthpiece assembly for establishing a protected airway for a patient having a head with a front and a back, a mouth, a tongue, upper and lower lips and upper and lower teeth, the mouthpiece assembly comprising:

a generally elliptical tubular bite block having a substantially vertical minor axis extending between opposing top and a bottom walls and having opposing forward and rearward ends and a generally elliptical passageway formed therethrough;

a generally elliptical front shield attached to the forward end of the tubular bite block portion, the front shield having a generally horizontal major axis extending between opposing edge portions, a central opening in communication with the passageway for receiving medical instruments therethrough and a strap opening adjacent each of the opposing edge portions, at least a portion of the front shield is curved rearward and is flexible to allow the at least a portion of the front shield to conform to the patient's facial structure;

a tongue depressing member extending rearwardly and downwardly from the rearward end of the bottom wall of the tubular bite block, the tongue depressing member being adapted for engaging the tongue of the patient and substantially preventing a forward portion of the tongue from moving rearward and blocking the patient's airway;

a resilient cushioning sleeve formed around at least a portion of the tubular bite block, the resilient cushioning sleeve being formed of a closed cell foam material and being adapted for receiving and engaging the patient's upper and lower teeth and the patient's upper and lower lips;

a substantially cylindrical plug formed from a resilient closed cell foam material, the plug being adapted for compression and insertion into the passageway to position and secure an instrument inserted through the passageway; and a headstrap having an elongate belt member with first and second ends adapted for insertion through the strap openings in the front shield and for fastening the belt member to the front shield, the belt member being adapted for engaging the back of the patient's head to secure the mouthpiece assembly in place.

2. A mouthpiece assembly according to claim 1 wherein the bite block, front shield and tongue depressing member are integrally formed as a single mouthpiece body.

3. A mouthpiece assembly according to claim 2 wherein the mouthpiece body is molded from a medical grade plastic material.

4. A mouthpiece assembly according to claim 1 wherein the front shield has a first side area intermediate the central opening and a first one of the opposing edge portions and a second side area intermediate the central opening and a second one of the opposing edge portions, a first cutout opening being formed in the first side area and a second cutout opening being formed in the second side area, the first and second cutout openings being arranged and configured to impart flexibility to the first and second side areas.

5. A mouthpiece assembly according to claim 4 wherein the front shield has an upper shield area above and adjacent the central opening and a lower shield area below and adjacent the central opening, the upper and lower shield areas being substantially rigid.

6. A mouthpiece assembly according to claim 1 further comprising at least one detent attached to an outer surface of the tubular bite block, the at least one detent being adapted for engaging an inner surface of the cushioning sleeve to inhibit movement of the cushioning sleeve along the outer surface of the tubular bite block.

7. A mouthpiece assembly according to claim 6 wherein the at least one detent has a triangular cross-section with a forward face set at a first angle relative to the outer surface and a rearward face set at a second angle relative to the outer surface, the second angle being shallower than the first angle so that forward motion of the cushioning sleeve relative to the outer surface is inhibited to a lesser degree than rearward motion of the cushioning sleeve relative to the outer surface.

8. A mouthpiece assembly according to claim 6 wherein a first strap opening is formed in the annular shield member intermediate the first one of the opposing edge portions and the first cutout opening and a second strap opening is formed in the annular shield member intermediate the second one of the opposing edge portions and the second cutout opening, the mouthpiece assembly further comprising:

a headstrap having a belt member with a first end adapted for insertion through the first strap opening and a second end adapted for insertion through the second strap opening and having means for fastening the first and second belt member ends to the annular shield member, the belt member being adapted for engaging a portion of the patient's head to secure the mouthpiece assembly in place.

9. A mouthpiece assembly according to claim 8 wherein the headstrap includes means for adjusting the length of the belt member.

10. A mouthpiece assembly for establishing a protected airway for a patient having a head with a front and a back, a mouth, a tongue, upper and lower lips and upper and lower teeth, the mouthpiece assembly comprising:

a tube member having a generally elliptical cross-section and having opposing top and bottom tube member walls extending between opposing forward and rearward tube member ends, the top and bottom walls defining a generally elliptical passageway extending along a centerline through the forward and rearward ends;

an annular shield member attached as a flange to the forward tube member end, the annular shield member being formed with a generally elliptical central opening in registration with the passageway, opposing edge portions spaced laterally outward from the central opening, a first side area intermediate the central opening and a first one of the opposing edge portions and a second side area intermediate the central opening and a second one of the opposing edge portions, a first cutout opening formed in the first side area, and a second cutout opening formed in the second side area, the first and second cutout openings being arranged and configured to impart flexibility to the first and second side areas; and a tongue depressing member attached to the bottom tube member wall and extending rearwardly and downwardly from the rearward tube member end, at least a portion of the tongue depressing member having a shallow, C-shaped cross-section configured to match and blend with a portion of the bottom tube member wall, the tongue depressing member being adapted for engaging the tongue of the patient to substantially prevent a portion of the tongue from moving rearward and blocking the patient's airway.

11. A mouthpiece assembly according to claim 10 wherein the tube member, annular shield member and tongue depressing member are integrally formed as a single mouthpiece body.

12. A mouthpiece assembly according to claim 11 wherein the mouthpiece body is molded from a medical grade plastic material.

13. A mouthpiece assembly according to claim 10 wherein the annular shield member has an upper shield area above and adjacent the central opening and a lower shield area below and adjacent the central opening, the upper and lower shield areas being substantially rigid.

14. A mouthpiece assembly according to claim 10 further comprising a cushioning sleeve surrounding at least a portion of the tube member.

15. A mouthpiece assembly according to claim 14 further comprising at least one detent attached to an outer surface of the tube member, the at least one detent being adapted for engaging an inner surface of the cushioning sleeve to inhibit movement of the cushioning sleeve along the outer surface of the tube member.

16. A mouthpiece assembly according to claim 15 wherein the at least one detent has a triangular cross-section with a forward face set at a first angle relative to the outer surface and a rearward face set at a second angle relative to the outer surface, the second angle being shallower than the first angle so that forward motion of the cushioning sleeve relative to the outer surface is inhibited to a lesser degree than rearward motion of the cushioning sleeve relative to the outer surface.

17. A mouthpiece assembly according to claim 10 further comprising
a plug formed from a resilient closed cell foam material, the plug being adapted for compression and insertion into the passageway to position and secure an instrument inserted through the passageway.

18. A mouthpiece assembly for establishing a protected airway for a patient having a head with a front and a back, a mouth, a tongue, upper and lower lips and upper and lower teeth, the mouthpiece assembly comprising:
a tube member having a generally elliptical cross-section and having opposing top and bottom tube member walls extending between opposing forward and rearward tube member ends, the top and bottom walls defining a generally elliptical passageway extending along a centerline through the forward and rearward ends;
an annular shield member attached as a flange to the forward tube member end, the annular shield member being formed with a generally elliptical central opening in registration with the passageway, opposing edge portions spaced laterally outward from the central opening, a first side area intermediate the central opening and a first one of the opposing edge portions and a second side area intermediate the central opening and a second one of the opposing edge portions, a first cutout opening formed in the first side area, and a second cutout opening formed in the second side area, the first and second cutout openings being arranged and configured to impart flexibility to the first and second side areas; and
means for engaging and depressing at least a portion of a patient's tongue when the tube member is inserted into the patient's mouth, the means for engaging and depressing being attached to the rearward tube member end and being adapted to substantially prevent a portion of the tongue from moving rearward and blocking the patient's airway.

19. A mouthpiece assembly according to claim 18 further comprising means for securing the mouthpiece assembly in place when the tube assembly is inserted into a patient's mouth, the means for securing being attached to the annular shield member.

20. A mouthpiece assembly according to claim 19 wherein the means for securing the mouthpiece assembly in place includes an adjustable headstrap adapted for engaging a portion of the patient's head to secure the mouthpiece assembly in place.

21. A mouthpiece assembly according to claim 18 further comprising cushioning means for receiving and engaging the patient's upper and lower teeth when the tube member is inserted into a patient's mouth, the cushioning means being disposed adjacent an outer surface of the tube member.

22. A mouthpiece assembly according to claim 21 wherein the cushioning means includes a foam sleeve disposed around at least a portion of the outer surface of the tube member, the mouthpiece assembly further comprising at least one detent attached to the outer surface of the tube member, the at least one detent being adapted for engaging an inner surface of the cushioning sleeve to inhibit movement of the cushioning sleeve along the outer surface of the tube member.

23. A mouthpiece assembly according to claim 22 wherein the at least one detent has a triangular cross-section with a forward face set at a first angle relative to the outer surface and a rearward face set at a second angle relative to the outer surface, the second angle being shallower than the first angle so that forward motion of the cushioning sleeve relative to the outer surface is inhibited to a lesser degree than rearward motion of the cushioning sleeve relative to the outer surface.

24. A mouthpiece assembly according to claim 18 further comprising means for positioning and securing an instrument inserted through the central opening and the elliptical passageway, the means for positioning and securing being removably secured within the elliptical passageway.

25. A mouthpiece assembly for establishing a protected airway for a patient having a head with a front and a back, a mouth, a tongue, upper and lower lips and upper and lower teeth, the mouthpiece assembly comprising:
a tube member having a generally elliptical cross-section and having opposing top and bottom tube member walls extending between opposing forward and rearward tube member ends, the top and bottom walls defining a generally elliptical passageway extending along a centerline through the forward and rearward ends;
a cushioning sleeve surrounding at least a portion of the tube member;
at least one detent attached to an outer surface of the tube member, the at least one detent being adapted for engaging an inner surface of the cushioning sleeve to inhibit movement of the cushioning sleeve along the outer surface of the tube member, the at least one detent having a triangular cross-section with a forward face set at a first angle relative to the outer surface and a rearward face set at a second angle relative to the outer surface, the second angle being shallower than the first angle so that forward motion of the cushioning sleeve relative to the outer surface is inhibited to a lesser degree than rearward motion of the cushioning sleeve relative to the outer surface;
an annular shield member attached as a flange to the forward tube member end, the annular shield member being formed with a generally elliptical central opening in registration with the passageway, opposing edge portions spaced laterally outward from the central opening, a first side area intermediate the central opening and a first one of the opposing edge portions and a second side area intermediate the central opening and a second one of the opposing edge portions; and
a tongue depressing member attached to the bottom tube member wall and extending rearwardly and downwardly from the rearward tube member end, the tongue depressing member being adapted for engaging the tongue of the patient to substantially prevent a portion of the tongue from moving rearward and blocking the patient's airway.

26. A mouthpiece assembly according to claim 25 wherein the tube member, the at least one detent, the annular shield member and the tongue depressing member are integrally formed as a single mouthpiece body.

27. A mouthpiece assembly according to claim 25 wherein the mouthpiece body is molded from a medical grade plastic material.

28. A mouthpiece assembly according to claim 25 wherein the annular shield member has a first cutout opening formed in the first side area and a second cutout opening formed in the second side area, the first and second cutout openings being arranged and configured to impart flexibility to the first and second side areas.

29. A mouthpiece assembly according to claim 28 wherein the annular shield member has an upper shield area above and adjacent the central opening and a lower shield area below and adjacent the central opening, the upper and lower shield areas being substantially rigid.

30. A mouthpiece assembly according to claim 25 wherein a first strap opening is formed in the annular shield member intermediate the first one of the opposing edge portions and the first cutout opening and a second strap opening is formed in the annular shield member intermediate the second one of the opposing edge portions and the second cutout opening, the mouthpiece assembly further comprising:

a headstrap having a belt member with a first end adapted for insertion through the first strap opening and a second end adapted for insertion through the second strap opening and having means for fastening the first and second belt member ends to the annular shield member, the belt member being adapted for engaging a portion of the patient's head to secure the mouthpiece assembly in place.

31. A mouthpiece assembly according to claim 30 wherein the headstrap includes means for adjusting the length of the belt member.

32. A mouthpiece assembly according to claim 25 further comprising:

a plug formed from a resilient closed cell foam material, the plug being adapted for compression and insertion into the passageway to position and secure an instrument inserted through the passageway.

33. A mouthpiece assembly according to claim 25 wherein at least a portion of the tongue depressing member has a shallow, C-shaped cross-section configured to match and blend with a portion of the bottom tube member wall.

* * * * *